United States Patent [19]

Saville

[11] Patent Number: Plant 5,471

[45] Date of Patent: May 21, 1985

[54] ROSE PLANT

[75] Inventor: F. Harmon Saville, Rowley, Mass.

[73] Assignee: Nor'East Miniature Roses, Inc., Rowley, Mass.

[21] Appl. No.: 556,265

[22] Filed: Nov. 30, 1983

[51] Int. Cl.[3] ..... A01H 5/00

[52] U.S. Cl. ..... Plt./10

[58] Field of Search ..... Plt./10

*Primary Examiner*—Robert E. Bagwill
*Attorney, Agent, or Firm*—Vincent G. Gioia

[57] ABSTRACT

A new miniature rose variety of currant red coloring long lasting on the plant and as a cut flower opening cup shaped and becoming flat.

1 Drawing Figure

The present invention relates to a new and distinct variety of rose plant of the miniature rose class, which was originated by my crossing as seed parent the rose known as "Tamango" (U.S. Plant Pat. No. 2,857) and the rose known as "Sheri Anne" (U.S. Plant Pat. No. 3,826) as pollen parent. The varietal denomination of this new variety is "Savmore".

Among the novel characteristics possessed by this new variety which distinguish it from its parents and all other varieties of which I am aware are its cup shaped current red flowers which become flat upon opening and which are long lasting on the plant and as cut flowers. The flowers are borne one to a stem and in small sprays. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (R.H.S.C.C.). The terminology used in color description herein refers to plate numbers in the aforementioned color chart, e.g., "46A" is plate 46A of The Royal Horticultural Society Color Chart.

Parentage: Seedling.
*Seed parent.*—"Tamango".
*Pollen parent.*—"Sheri Anne".
Class: Miniature.

The following observations are made of specimens grown outdoors in Essex County, Mass., during the month of October.

FLOWER

Blooming habit: Recurrent.
Bud:
(1) *Size.*—Medium.
(2) *Form.*—Short, pointed.
(3) *Color.*—When sepals first divide — currant red near 46A. When petals begin to unfurl — near 46A to 46B.
(4) *Sepals.*—Longer than bud, slightly bearded.

(5) *Peduncle.*—Length — $\frac{1}{2}$ to $\frac{3}{4}$ inch. Aspect — straight. Strength — erect. Color — near 146C.

Bloom:
(1) *Size.*—Average size when fully expanded — about 1 to $1\frac{1}{4}$ inches.
(2) *Borne.*—Singly and several together in small sprays.
(3) *Form.*—Cupped at first, becoming flat, most petals reflex upon opening.
(4) *Petalage.*—Number of petals under normal conditions — about 30.
(5) *Color.*—As currant red buds 46A unfurl color remains stable between 46A to 46B with petal underside surface slightly lighter 47B. Some of the outer petals blacken at petal edge. Color generally holds upon aging. Color at point of petal attachment is near 150D.

Petals:
(1) *Texture.*—Thick, stiff, good substance.
(2) *Appearance.*—Inside — satiny, outside — matte.
(3) *Form.*—Narrow, pointed, ovate.
(4) *Arrangement.*—Regularly arranged, shingle-like.
(5) *Petaloids in center.*—Few.
(6) *Persistence.*—Persistent then drop off cleanly.
(7) *Fragrance.*—Slight.
(8) *Lasting quality.*—Very long lasting on plant and as cut flower.

REPRODUCTIVE ORGANS

Stamens, filaments and anthers:
(1) *Arrangement.*—Regularly arranged around styles.
(2) *Color.*—Near 13B.

Pollen:
*Color.*—Near 13B.
Styles: Uneven, medium length
Stigmas:
*Color.*—Near 157B.

Hips:
*Shape.*—Slightly elongated, oval.
*Size*—About $\frac{3}{8}$ inch.
*Color.*—Orange red.
*Do seeds protrude.*—No.

PLANT

Form: Compact, bushy.
Growth: Vigorous.
*Height attained.*—About 14 to 16 inches.
Foliage: Compound 5 to 7 leaflets.

(1) *Size.*—Medium.

(2) *Quantity.*—Very abundant.

(3) *Color.*—New foliage: Upper side — near to 146A edged 178A. Under side — near to 146D. Old foliage: Under side — near 133A. Under side — near 138C.

(4) *Shape.*—Ovate.

(5) *Texture.*—Upper side is semi-glossy and under side is matte.

(6) *Edge.*—Serrated.

(7) *Serration.*—Serrate.

(8) *Leaf stem.*—Color — near to 147B. Under side — near 146D.

(9) *Stipules.*—Medium, not bearded.

(10) *Resistance to disease.*—Blackspot — average. Mildew — average. Rust — average.

Wood:

(1) *New wood.*—Color — near 185A. Bark — smooth.

(2) *Old wood.*—Color — near 138B. Bark — smooth.

Thorns:

(1) *Thorns.*—Quantity (main stalk): ordinary. On laterals from stalk — ordinary. Form — short, straight, thin, pointed, slanted slightly downward. Length — short. Color — near 182A. Position — irregular.

(2) *Prickles.*—None.

Winter hardiness: Requires ordinary protection in extreme climates.

I claim:

1. A new and distinct variety of rose plant of the miniature rose class, substantially as shown and described, characterized particularly by currant red flowers which are very long lasting on the plant and after cutting, are initially cupped and then become flat upon opening and bloom one to a stem and in small sprays and retain their color upon aging.

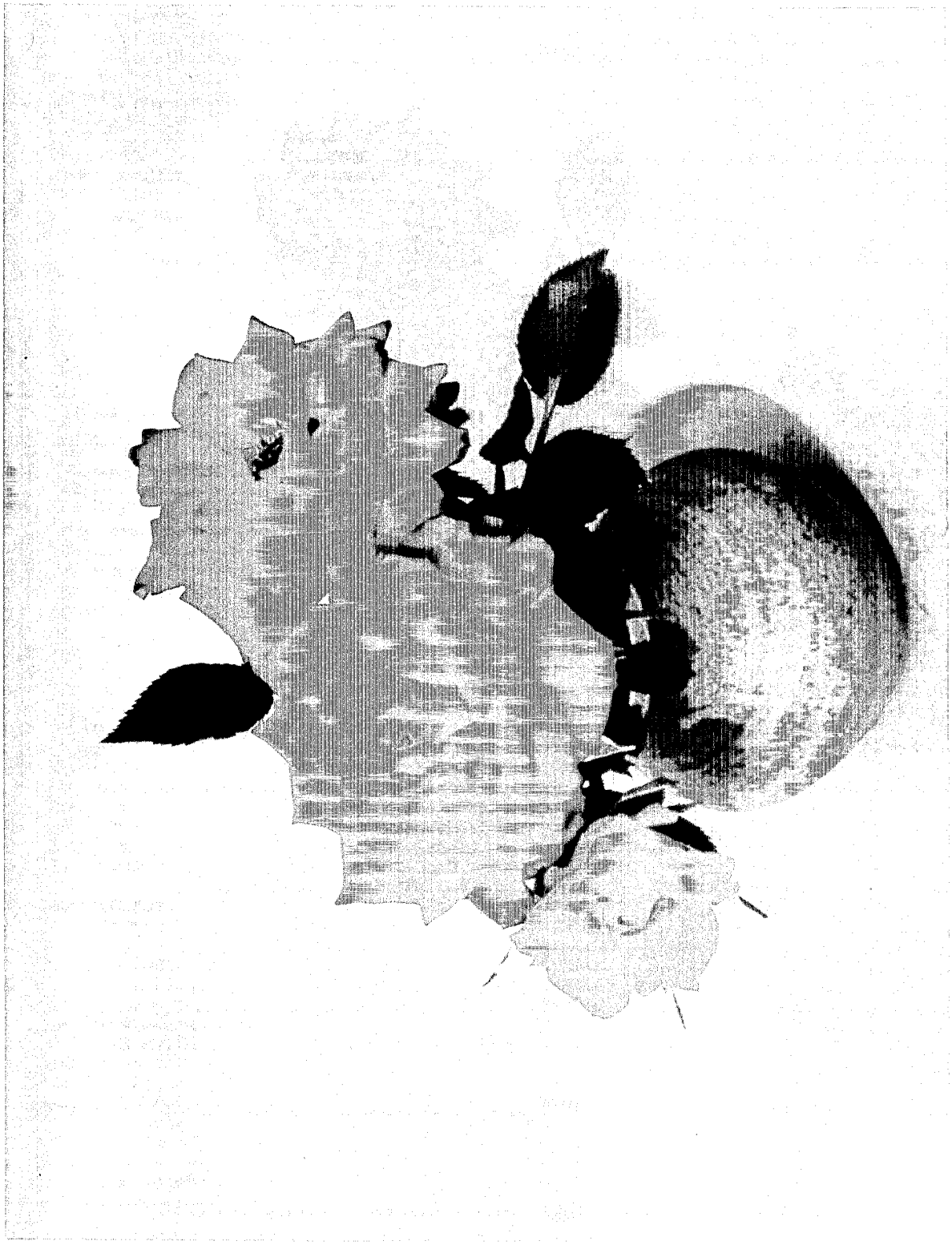

* * * * *